United States Patent [19]

Davis et al.

[11] Patent Number: 4,992,265

[45] Date of Patent: Feb. 12, 1991

[54] METHODS AND COMPOSITIONS FOR INCREASING THE DIAMETER OF THE HAIR COMPRISING RETINOL ESTERS

[75] Inventors: Walter B. Davis; Margaret D. Batt; Benjamin D. Ridge, all of Weybridge, England

[73] Assignee: Beecham Group p.l.c., England

[21] Appl. No.: 314,754

[22] Filed: Feb. 23, 1989

[30] Foreign Application Priority Data

Feb. 25, 1988 [GB] United Kingdom ................. 8804419
Aug. 19, 1988 [GB] United Kingdom ................. 8819738

[51] Int. Cl.$^5$ ............................................. A61K 7/06
[52] U.S. Cl. ...................................... 424/70; 514/725
[58] Field of Search .......................... 514/725; 424/70

[56] References Cited

U.S. PATENT DOCUMENTS

| | | | |
|---|---|---|---|
| 3,932,634 | 1/1976 | Kardys | 514/725 X |
| 4,170,229 | 10/1979 | Olson | 128/67 |
| 4,201,235 | 5/1980 | Ciavatta | 424/70 |
| 4,333,924 | 6/1982 | Bowley et al. | 424/170 |
| 4,727,088 | 2/1988 | Scott et al. | 514/725 |
| 4,826,828 | 5/1989 | Wilmott et al. | 514/725 X |
| 4,834,076 | 5/1989 | Millet et al. | 128/65 |
| 4,839,164 | 6/1989 | Smith | 424/70 X |

FOREIGN PATENT DOCUMENTS

| | | |
|---|---|---|
| 094771 | 11/1983 | European Pat. Off. |
| 0107885 | 5/1984 | European Pat. Off. |
| 330496 | 8/1989 | European Pat. Off. |
| 216812 | 12/1984 | Japan |
| 183206 | 8/1986 | Japan |
| 1487543 | 10/1977 | United Kingdom |
| 1489133 | 10/1977 | United Kingdom |
| 2833 | 9/1982 | World Int. Prop. O. ............. 424/70 |

OTHER PUBLICATIONS

Patent Abstracts of Japan of JP-A-59 216 812 12/06/1984.
Patent Abstracts of Japan of JP-A-61 183 206 08/15/1986.

*Primary Examiner*—Merrell C. Cashion, Jr.
*Assistant Examiner*—Susan S. Rucker
*Attorney, Agent, or Firm*—Jacobs & Jacobs

[57] ABSTRACT

A hair care composition comprising at least 1,000 IUg$^{-1}$ of an ester of retinol in a topically acceptable carrier is useful for increasing the diameter of growing hair.

31 Claims, No Drawings

METHODS AND COMPOSITIONS FOR INCREASING THE DIAMETER OF THE HAIR COMPRISING RETINOL ESTERS

This invention relates to topical hair treatment compositions containing derivatives of Vitamin A (retinol).

It is known to use retinoic acid, that is Vitamin A acid, to increase the growth of human scalp hair. However, retinoic acid is a known irritant and its use in formulations has been associated with such problems. Certain retinoic acid derivatives have also been shown to be effective in increasing the rate of hair growth by prolonging the anagen phase of the hair cycle.

WO-82 02833 describes a method for increasing the rate of growth of hair and prolonging the anagen phase of the hair cycle by topically administering retinoic acid or one of its derivatives to the scalp in an effective amount. Administration of these compositions is topically, by lotions, ointments and creams.

U.S. Pat. No. 4,170,229 describes the prevention of hair loss by the topical administration of retinyl palmitate in the form of an aqueous sprayable emulsion.

GB-1,487,543 describes a water based dermatological ointment comprising from 0.1 to 0.3% by weight of retinyl palmitate in admixture with ichthyol, dexamethasone and salicyclic acid, used for the treatment of alopecia seborrhoeica.

It has now surprisingly been found that retinol esters are effective in increasing the diameter of growing hair. These esters, unlike retinoic acid, show very low irritancy when formulated.

It has also surprisingly been found that the stability of retinol esters for use in hair-care products can be enhanced by the selection of an appropriate carrier.

According to the present invention there is provided a hair care composition comprising at least 1,000 $IUG^{-1}$ of an ester of retinol (not being retinyl palmitate), or of a mixture of esters of retinol (at least one of which is not retinyl patmitate), in a topically acceptable carrier.

In a further aspect of the invention there is provided a hair care composition comprising at least 1,000 $IUg^{-1}$ of an ester of retinol, or of a mixture of esters of retinol, in a topically acceptable carrier which is anhydrous or wherein the retinol ester or mixture thereof is dissolved in the oil phase of a multiphase system, such as an oil-in-water or water-in-oil emulsion.

Preferably the oil is a volatile oil such as a volatile silicone.

A further aspect of the invention provides a method of increasing the diameter of growing hair e.g. human scalp hair which method comprises the topical administration of an effective amount of an ester of retinol (not being retinyl palmitate), or of a mixture of esters of retinol (at least one of which is not retinyl palmitate), or of a composition in accordance with the invention.

These compositions can be applied topically in the form of lotions, creams conditioners, gels or mousses. However, topical administration should not just be limited to those mentioned above.

Preferably the composition comprises from 1,000 to 15,000 $IUg^{-1}$ of at least one fatty acid ester of retinol, more preferably from 2,000 to 7,000 $IUg^{-1}$.

Preferably, the composition of the invention comprises at least one $C_{2-16}$, more especially $C_{3-10}$, alkanoyl ester of retinol.

Preferably, the composition of the invention comprises at least one $C_{3-7}$ straight chain, branched chain, or cyclo alkanoyl ester of retinol for example retinyl propionate, butyrate, cyclopentanecarboxylate, pivalate, valerate, hexanoate or heptanoate. The preferred composition comprises the propionate or the palmitate.

An advantage of the present invention is that an increase in the thickness of the hair shaft is achieved without any decrease in the colour density of the hair, so that areas of thinning hair are effectively disguised.

The hair treatment composition is preferably a 'leave-on' product, and includes conditioners, tonics, lotions, creams, dressings, gels, spray on conditioners, aerosol conditioning sprays, mousses, post foaming hair gels, styling and hairsprays.

According to the type of product required, in addition, to the retinol ester(s), many other cosmetically acceptable ingredients may be used.

For example, an oil-in-water emulsion may be prepared containing 5 to 50% by weight of oil. Examples of oils suitable for inclusion in the present compositions include: volatile linear iso-paraffins, acyclic dimethylpolysiloxanes, cyclic dimethylpolysiloxanes, mineral oils, synthetic fatty acid esters, fatty alcohols, lanolin and its derivatives.

Anhydrous hair formulations that do not contain any water are also included in this invention, such as oil based hair tonics containing up to 99% oil and an optional additional amount of an anhydrous alcohol.

Preferably the oils used are volatile, such as volatile silicones e.g. D.C. 345.

In a particularly preferred aspect of the invention, retinyl palmitate is formulated with a hair tonic comprising a volatile silicone and/or an anhydrous alcohol.

Gels, conditioners and other hair dressings will contain ingredients conventionally used in the art, and may include emulsifiers, detergents and alcohol. Additional ingredients such as perfumes and dyes may also be used.

The compositions of this invention should desirably include an anti-oxidant effective in preventing oxidation of the retinol ester and consequent reduction in the activity of the composition. Some anti-oxidants are effective in this respect but themselves oxidise to give a noticeable yellowing of the products.

Two anti-oxidants which are particularly suitable for incorporation are butylated hydroxytoluene (BHT), (2,3-di-tert-butyl-p-cresol) and butylated hydroxyanisole (BHA), (2-tert-butyl-4-hydroxyanisole or 3-tert-butyl-4-hydroxyanisole or a mixture of these. Accordingly in another of its aspects, the invention includes a composition in accordance with the invention including BHT and/or BHA as anti-oxidant.

The following Examples are prepared in accordance with the present invention.

EXAMPLE 1

| Silicone Emulsion | % w/w |
| --- | --- |
| *Silicone Emulsion Q2.3225C | 10.00 |
| *Silicone DC 345 | 10.00 |
| Sodium Chloride | 1.00 |
| Retinyl Propionate | 0.15 |
| Perfume | qs |
| Preservative | qs |
| Deionised Water to | 100.00 |

*Q2-3225C - volatile silicone self emulsifying CTFA name Cyclomethicone (and) Dimethicone Copolyol
*DC 345 CTFA name Cyclomethicone

EXAMPLE 2

| Hair Tonic (oil based) | % w/w |
| --- | --- |
| Mineral Oil to | 100.00 |
| Arlacel 186 | 1.50 |
| Aduvex 248 (UV absorber) | 0.15 |
| Retinyl propionate | 0.15 |
| Perfume | 0.50 |

EXAMPLE 3

A 2-layer hairdressing composition was prepared using 70% of the aqueous phase phase and 30% of the oil phase

|  | % w/w |
| --- | --- |
| Oil phase |  |
| Mineral oil to | 100.00 |
| Retinyl propionate | 0.51 |
| Perfume | qs |
| Dyes | qs |
| Aqueous phase |  |
| Ethanol | 20.00 |
| Perfume | qs |
| Boric acid | 1.00 |
| Protein hydrolysate | 1.40 |
| Sodium chloride | 0.50 |
| Dyes | qs |
| Deionised water to | 100.00 |

EXAMPLE 4

| Grooming Gel | % w/w |
| --- | --- |
| Carbopol 940 | 0.70 |
| Triethanolamine | 0.40 |
| Glycerine | 13.50 |
| Propylene Glycol | 4.00 |
| *Silicone DC 193 | 0.50 |
| Dowicil 200 (Preservative) | 0.20 |
| Mineral Oil | 20.00 |
| Retinyl propionate | 0.15 |
| BHA or BHT | 0.20 |
| Deionised water to | 100.00 |

*DC 193 CTFA name Dimethicone Copolyol.

EXAMPLE 5

| Gel hairdressing | % w/w |
| --- | --- |
| Carbopol 940 | 0.70 |
| Triethanolamine | 0.40 |
| Mineral Oil | 20.00 |
| Dowicil 200 (Preservative) | 0.20 |
| Retinyl propionate | 0.15 |
| BHA or BHT | 0.20 |
| Perfume | qs |
| Dyes | qs |
| Deionised water to | 100.00 |

EXAMPLE 6

| Non-oily Scalp Tonic | % w/w |
| --- | --- |
| Silicone DC 345 | 34.00-98.85 |
| Propylene Glycol | 1.00 |
| Retinyl palmitate | 0.15 |
| Perfume | qs. |
| Dyes | qs. |
| Anhydrous alcohol (optional) to | 100.00% |

The active retinyl palmitate is slowly dissolved in the silicone oil and the remaining ingredients are incorporated in a conventional manner.

EXAMPLE 7

| Non-oily Scalp Tonic | % w/w |
| --- | --- |
| Silicone DC 345 fluid | 34.00-98.85 |
| Propylene Glycol | 1.00 |
| Retinyl propionate | 0.15 |
| Perfume | qs |
| Dyes | qs |
| Anhydrous alcohol (optional) to | 100.00% |

The scalp tonic is prepared in accordance with the procedure outlined in Example 6.

We claim:

1. A method of increasing the diameter of growing hair, which comprises the topical administration of an effective amount of an ester of retinol, or of a mixture of esters of retinol at least one of which is not retinyl palmitate.

2. The method according to claim 1, wherein retinol ester or mixture of retinol esters in a $C_{3-10}$ alkanoyl ester of retinol or a mixture of $C_{3-10}$ alkanoyl esters of retinol.

3. The method according to claim 2, wherein said retinol ester is retinol propionate.

4. The method of increasing the diameter of growing hair, which comprises the topical administration of an effective amount of a hair care composition comprising at least 1,000 $IUg^{-1}$ of a $C_{3-10}$ alkanoyl ester of retinol or a mixture of $C_{3-10}$ alkanoyl esters of retinol in a topically acceptable carrier.

5. The method according to claim 4, wherein the ester of retinol is retinol propionate.

6. The method according to claim 4, wherein the composition comprises 1,000 to 15,000 $IUg^{-1}$ of at least one $C_{3-10}$ alkanoyl ester of retinol.

7. The method according to claim 4, wherein the topically acceptable carrier is anhydrous.

8. The method according to claim 7, wherein the ester of retinol is retinol propionate.

9. The method according to claim 7, wherein the composition comprises 1,000 to 15,000 $IUg^{-1}$ of at least one $C_{3-10}$ alkanoyl ester of retinol.

10. The method according to claim 7, wherein said composition is an anhydrous hair tonic containing an oil and/or an anhydrous alcohol.

11. The method according to claim 10, wherein the oil is a volatile silicone.

12. A method of increasing the diameter of growing hair, which comprises the topical application of a hair care composition comprising at least 1,000 $IUg^{-1}$ of an ester of retinol, or a mixture of esters of retinol, in a topically acceptable carrier which is anhydrous or wherein the retinol ester or mixture thereof is dissolved in the oil phase of a mulitphase system, such as an oil-in-water or water-in-oil emulsion.

13. The method according to claim 12, wherein the ester of retinol is retinol propionate.

14. The method according to claim 12, wherein the composition comprises 1,000 to 15,000 $IUg^{-1}$ of at least one $C_{3-10}$ alkanoyl ester of retinol.

15. The method according to claim 12, wherein the topically acceptable carrier is anhydrous.

16. The method according to claim 15, wherein said composition is an anhydrous hair tonic containing an oil and/or an anhydrous alcohol.

17. The method according to claim 16, wherein the oil is a volatile silicone.

18. A method of increasing the diameter of growing hair, which comprises the topical application of a hair care composition comprising at least 1,000 $IUg^{-1}$ of a $C_{2-16}$ alkanoyl ester of retinol, or a mixture of $C_{2-16}$ alkanoyl esters of retinol, in a topically acceptable carrier wherein the retinol ester or mixture thereof is dissolved in the oil phase of a multiphase system, such as an oil-in-water or water-in-oil emulsion.

19. The method according to claim 18, wherein the oil is a volatile silicone.

20. The method according to claim 18, wherein the composition comprises 1,000 to 15,000 $IUg^{-1}$ of at least one $C_{2-16}$ alkanoyl ester of retinol.

21. A hair care composition comprising at least 1,000 $IUg^{-1}$ of a $C_{3-10}$ alkanoyl ester of retinol or a mixture of $C_{3-10}$ alkanoyl esters of retinol in a topically acceptable carrier.

22. A composition according to claim 21, wherein the ester of retinol is retinol propionate.

23. A composition according to claim 21, comprising 1,000 to 15,000 $IUg^{-1}$ of at least one $C_{3-10}$ alkanoyl ester of retinol.

24. A composition according to claim 21, wherein the optically acceptable carrier is anhydrous.

25. A composition according to claim 24, wherein the ester of retinol is retinol propionate.

26. A composition according to claim 24, comprising 1,000 to 15,000 $IUg^{-1}$ of at least one $C_{3-10}$ alkanoyl ester of retinol.

27. A composition according to claim 24, which is an anhydrous hair tonic containing an oil and/or an anhydrous alcohol.

28. A composition according to claim 27, wherein the oil is a volatile silicone.

29. A hair care composition comprising at least 1,000 $IUg^{-1}$ of a $C_{2-16}$ alkanoyl ester of retinol, or a mixture of $C_{2-16}$ alkanoyl esters of retinol, in a topically acceptable carrier wherein the retinol ester or mixture thereof is dissolved in the oil phase of a multiphase system, such as an oil-in-water or water-in-oil emulsion.

30. A composition according to claim 29, wherein the oil is a volatile silicone.

31. A composition according to claim 29, comprising 1,000 to 15,000 $IUg^{-1}$ of at least one $C_{2-16}$ alkanoyl ester of retinol.

* * * * *